United States Patent
Land, III

(10) Patent No.: US 7,749,443 B2
(45) Date of Patent: Jul. 6, 2010

(54) ENHANCED SAMPLING DEVICE

(75) Inventor: H. Bruce Land, III, Laurel, MD (US)

(73) Assignee: The Johns Hopkins University, Baltimore, MD (US)

( * ) Notice: Subject to any disclaimer, the term of this patent is extended or adjusted under 35 U.S.C. 154(b) by 416 days.

(21) Appl. No.: 11/957,837

(22) Filed: Dec. 17, 2007

(65) Prior Publication Data

US 2009/0199621 A1 Aug. 13, 2009

(51) Int. Cl.
*G01N 30/96* (2006.01)
*G01N 30/02* (2006.01)
*G01N 1/00* (2006.01)

(52) U.S. Cl. .......................... 422/69; 422/70; 73/23.41; 73/864.85; 73/864.86; 73/864.87; 436/178; 210/634; 96/101

(58) Field of Classification Search .................. 422/69; 73/23.41
See application file for complete search history.

(56) References Cited

U.S. PATENT DOCUMENTS

| | | | |
|---|---|---|---|
| 5,691,206 A | 11/1997 | Pawliszyn | |
| 6,042,787 A | 3/2000 | Pawliszyn | |
| 6,164,144 A * | 12/2000 | Berg | 73/863.21 |
| 6,481,301 B2 | 11/2002 | Pawliszyn | |
| 6,537,827 B1 | 3/2003 | Pawliszyn | |
| 6,719,826 B2 * | 4/2004 | Sasano et al. | 95/87 |
| 7,131,341 B2 * | 11/2006 | Wareham et al. | 73/864.71 |
| 2005/0011831 A1 * | 1/2005 | Pawliszyn | 210/634 |
| 2005/0142039 A1 * | 6/2005 | Chen et al. | 422/101 |

OTHER PUBLICATIONS

SPME Portrable Field Sampler with 100um PDMS Fiber, SUPELCO,Product Spec. 1977 Sigma-Aldrich Co.; Bulletin 925B, 2001 Sigma-Aldrich Co.; Bulletin 922, 1998 Sigma-Aldrich Co.

* cited by examiner

*Primary Examiner*—Jill Warden
*Assistant Examiner*—Jennifer Wecker
(74) *Attorney, Agent, or Firm*—Francis A. Cooch

(57) ABSTRACT

The present invention is directed to an enhanced sampling device, herein referred to as an ESD, for enhancing the collection efficiency of the SPME method by enhancing the flow of the analytes onto the sampling fiber. The ESD includes a tubular main body, used for a sampling shroud, which directs a flow of analytes to contact the fiber during collection. One end of the main body is open and faces the sample, allowing analytes to flow into the ESD and contact the fiber. A second piece of tubing branches from the other end of the main body and becomes an outlet port, possibly leading to a pump. The ESD permits more rapid transport and absorption of the analytes to the fiber for collection.

11 Claims, 2 Drawing Sheets

ENHANCED SAMPLING DEVICE

STATEMENT OF GOVERNMENTAL INTEREST

This invention was made with Government support under Department of the Navy contract N00024-03-D-6606. The Government has certain rights in the invention.

CROSS-REFERENCE TO RELATED APPLICATIONS

This application relates to U.S. provisional application No. 60/854,126, filed on Oct. 25, 2006, which is incorporated herein by reference in its entirety.

BACKGROUND OF THE INVENTION

1. Field of the Invention

The present invention relates to a device for enhancing the collection efficiency of the Solid Phase Microextraction (SPME) method of sample concentration, collection and injection for analysis by gas chromatography or liquid chromatography. More specifically, it relates to a device for enhancing the collection efficiency of the SPME method, which enhances the flow of the analytes onto the sampling fiber.

2. Description of the Related Art

Historically, the chief method of analyzing trace chemicals, also known as "analytes", was to employ a syringe to collect a sample of the analyte and then inject it into a gas chromatograph (GC) or liquid chromatograph (LC). This resulted in the capture and injection of only small quantities of the analytes and thus yielded poor sensitivity. It was discovered that if large quantities of vapor or liquid analyte were drawn through a treated filter the components of interest would be concentrated on the filter paper. Solvents were used to selectively remove the chemicals of interest from the filter and a small portion of the solvent containing the traces was then injected into the GC or LC. Concentration of the sample via a filter was an improvement in sensitivity over straight analyte injection, but it added many processing steps to the analysis, which could increase errors.

It was further discovered that gas samples could be drawn through tubing containing packing material, such as Tenax, to concentrate the sample on the packing. After sampling, the tubing was connected to the sampling inlet of the GC. If the packing was rapidly heated it would drive off the trace chemicals into the GC for analysis. This process was simpler than the filter process and yielded similar sample concentration enhancements as the filter paper method without the solvent extraction problems. However, this process was only compatible with GC techniques and not LC techniques.

Certain materials selectively adsorb and absorb materials based upon their chemical properties. For instance, silica gel will absorb water and then release it when heat is applied. Other extraction materials will release to certain solvents. Solid phase extraction (SPE) is a process which may employ selective adsorbents and solvents to concentrate the components of interest within the sample and selectively remove components that may interfere with later analysis. SPE can be a known effective alternative to liquid-to-liquid extraction in the analysis of aqueous samples. SPE reduces the consumption of high purity solvents and also reduces the time required to isolate the analytes of interest. However, the fact that SPE continues to use solvents has a number of disadvantages, notable among them being the need to take extensive precautions to guard against interference of the solvent with the analytes in the analyses.

Solid phase microextraction (SPME) is a similar process which allows the concentration of volatile or nonvolatile compounds from liquid samples or from headspace gas without the complicated apparatus and solvents of SPE. SPME may use a fiber mounted within a hollow needle sheath of a syringe. The fiber acts as a sponge which captures and concentrates the analytes. The fiber can then be inserted into the heated injector of a GC where the analytes may be thermally desorbed from the fiber and made available for analysis by the GC. SPME can achieve detection limits down to the parts-per-trillion range for a wide variety of compounds.

FIG. 1 is a cross-sectional view of one SPME device 10 in a retracted position and adjacent to a sample vessel 20. A thin fiber 30 may be coated with a substance that can enhance the selective absorption of the analytes, typically based upon the polarity of the molecules. Fiber 30 is attached to one end of a rod 40, with the other end of rod 40 being attached to plunger 50. Fiber 30 may be positioned inside of the needle sheath 60. Needle sheath 60 may be attached to cylinder 70. In the retracted position, cylinder 70 contains plunger 50 and partially contains rod 40, allowing them to potentially move longitudinally therein as a force is applied to plunger 50 along its main axis. SPME holder 80 is generally cylindrical in shape and includes a septum 90 at one end and a rod support and seal 91 at the other end. Needle sheath 60 containing fiber 30 is positioned inside SPME holder 80 and adjacent to septum 90. Sample vessel 20 may contain the material to be sampled, solid, liquid or gas, and may include a septum 100.

In operation, septum 90 of SPME holder 80 may be placed adjacent to septum 100 of sample vessel 20. Cylinder 70 can be depressed, thus injecting needle sheath 60 into sample vessel 20, as shown in FIG. 2. Next, plunger 50 is depressed which may extend fiber 30 through the free end of needle sheath 60, and thus may expose fiber 30 to the liquid or headspace gas within the vessel, as shown in FIG. 3. In this manner, fiber 30 is likely not damaged by unwanted contact. The analytes diffuse onto the surface of fiber 30 where they can be absorbed. Once enough time has elapsed to allow sufficient sample to be captured by fiber 30, fiber 30 is retracted into needle sheath 60 by retracting plunger 50 and needle sheath 60 is retracted via cylinder 70. Having the fiber containing the analyte sealed behind septum 90 prevents contamination of the fiber and may prevent escape of the analyte. Using a similar process, fiber 30 can be then be inserted into the GC sample inlet (not shown). The analytes are then removed from fiber 30 by thermal desorption and injected into a GC or LC for analysis. Since fiber 30 can be protected by septum 90 while retracted inside of SPME holder 80, this process protects fiber 30 while transporting field samples to a laboratory for the most detailed analyses.

While the SPME process accomplishes its intended purposes of concentrating and collecting materials of interest, it suffers from a number of drawbacks. First, the SPME process is dependent upon diffusion to transport the analytes from solid or liquid on the bottom of the vessel to the fiber for collection. Since the time for diffusion and absorption of the analytes depends on many factors (e.g. the analytes themselves, as well as the type and thickness of any coating on the fiber), this process can take hours and even days to accomplish. Such long sampling times have been problematic because adsorption is a bi-directional process and, therefore, with a long sampling time, the analyte being adsorbed also begins to desorb from the fiber resulting in a non-linear response and making quantization difficult. Therefore, techniques have been developed to reduce the absorption time.

For example, it is known that stirring and/or forceful agitation or heat may be applied to the sample vessel to reduce the absorption time. Stirring can be accomplished through the placement of a magnetic bar within the analyte and the use of a standard magnetic stirrer. Another method of agitation is to apply ultrasonic vibrations to the vial. However, agitation techniques can lead to damage to sample vials, damage to the fiber and also to damage to mechanical and electrical parts. Moreover, stirring techniques, whether they are magnetic, ultrasound or other methods, often increase the risk of contamination. Also, heat applied, either directly or as a side-effect of forceful agitation, leads to a rise in the temperature of the sample. Since adsorption efficiency is temperature-dependent, this introduces an unwanted variable into the analysis. SPME can be very effective in allowing the identification of trace compounds due to its ability to selectively concentrate the analyte. However, there are so many variable affecting the capture efficiency of the SPME that absolute quantitative analysis can be very difficult.

In the prior art, improvements on the SPME device have been proposed. For example, U.S. Pat. No. 7,131,341 to Wareham and Persaud discloses an instrument into which an SPME fiber and needle sheath is inserted. The holder/case contains a motor to present the fiber to the sample and retract the fiber into the needle sheath. This patent indicates that once the sample is on the fiber, the SPME can be either exchanged for a fresh one or immediately analyzed in the Wareham hosing. This patent is focused upon on-the-spot analysis of odor samples to determine if mold is within a wall or fungus samples to determine tree rot. This application is distinctly different than that of taking the SPME sample back to a lab for a more detailed analysis. First, if the SPME is removed from its housing for later analysis, as it is no longer sealed, it will likely leach sample and gather contamination. Though this patent discusses a tagging method, this tagging method appears incompatible with standard SPME holders, and thus leaves unaddressed a desirable next step of injecting the SPME into the laboratory analyzer for high resolution analysis. Further, this approach does not allow traceability of the analysis results to the quantity of air processed.

In order to overcome these problems, what is needed is a device to enhance the efficiency of the SPME process, the device permitting more rapid transport and absorption of the analytes to the fiber for collection. Further, the device must allow injection of the SPME into a full-scale laboratory analyzer. These features thus address and solve problems associated with conventional SPME systems.

SUMMARY OF THE INVENTION

The present invention is directed to an enhanced sampling device, herein referred to as an ESD, for enhancing the collection efficiency of the SPME method by enhancing the flow of the analytes onto the sampling fiber. The ESD includes a tubular main body, which may be used for a sampling shroud which directs a flow of analytes to contact the fiber during collection. One end of the main body can be open and may face the sample, allowing analytes to flow into the ESD and contact the fiber. A second piece of tubing may branch from the other end of the main body and can become an outlet port, possibly leading to a pump. This application describes several embodiments of the ESD. The ESD permits more rapid transport and absorption of the analytes to the fiber for collection by potentially passing the gas carrying the analyte coaxially over all surfaces of the SPME fiber in a closely confined area so that the majority of the analyte comes into intimate contact with the fiber where it may be captured for later analysis.

It is an object of the invention disclosed herein to provide a new and improved device for the SPME technique, which provides novel utility and flexibility through the use of a unique design which permits more rapid transport and absorption of analytes from solid, liquid or gas to the fiber for collection.

It is another object of the invention disclosed herein to provide a new and improved device for the SPME technique, which provides novel utility and flexibility through the use of a unique design which permits efficient collection of sample from a sample vessel or from ambient fluids, and in particular gases.

It is an advantage of the invention disclosed herein to provide a new and improved device for the SPME technique, which does not agitate or stir the sample.

It is a further advantage of the invention disclosed herein to provide a new and improved device for the SPME technique, which does not add additional heat to the sample.

It is a further advantage of the invention that it constantly passes fresh gaseous sample containing the analyte in close proximity to the SPME fiber and that the flow rate and time of the flow can be easily measured which permits quantitation such that the results of the analysis can specify the quantity of analyte per volume of gas (i.e. ppm/liter).

It is a further advantage of the invention that the required sampling time is reduced by more than 50%.

It is a further advantage of the invention that due to the decrease in sampling time the linearity of the SPME technique is improved.

These and other objects and advantages of the present invention will be fully apparent from the following description, when taken in connection with the annexed drawings.

BRIEF DESCRIPTION OF THE DRAWINGS

The teachings of the present invention can be readily understood by considering the following detailed description in conjunction with the accompanying drawings, in which.

DETAILED DESCRIPTION OF EXEMPLARY EMBODIMENTS

Reference will now be made in detail to the exemplary embodiments of the present application, examples of which are illustrated in the accompanying drawings. It should be noted that both absorption and adsorption can occur on the sampling fiber. One process will predominate over the other depending upon the type of material on the fiber and the type of chemical being sampled.

Figure 1:
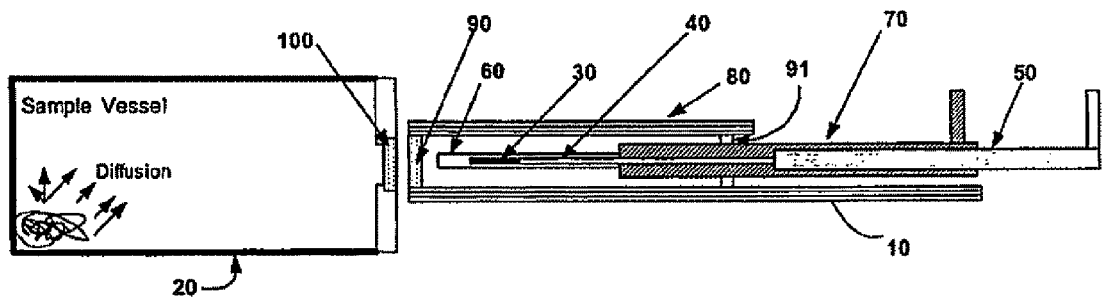
FIG. 1 is a cross-sectional view of a conventional SPME device in a retracted position.
Figure 2:
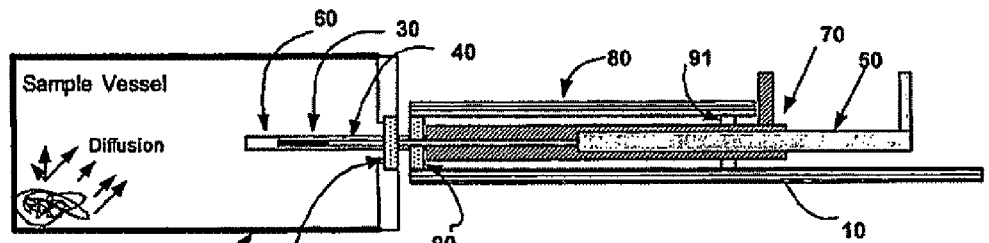
FIG. 2 is a cross-sectional view of a conventional SPME device in a partially extended position.
Figure 3:
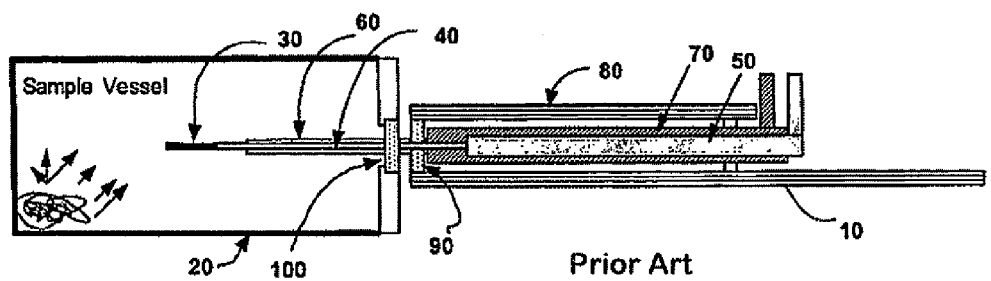
FIG. 3 is a cross-sectional view of a conventional SPME device in a fully extended position.
Figure 4:
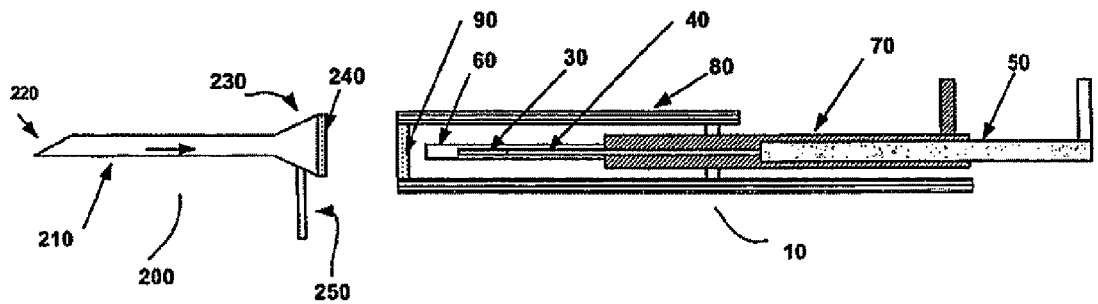
FIG. 4 is a cross sectional view of a first embodiment of an ESD for a SPME according to the principles of the present application.

FIG. 4 shows a cross-sectional view of a first embodiment of an ESD according to the principles of the present application. FIG. 4 shows the relative position of SPME 10 and ESD 200 prior to insertion of needle sheath 60 into ESD 200, while SPME 10 is in a fully retracted position. In this embodiment, ESD 200 is a stand alone device, and is not attached to SPME 10. ESD 200 includes a main body 210, in a generally tubular shape and having two ends. The first end 220 is open and serves as a sample inlet, permitting sample to flow into main body 210. Note that in FIG. 4 sample inlet 220 is shown having a shape cut at an angle of approximately 45 degrees to the body axis of main body 210. This particular shape is for illustrative purposes only and is not intended to limit the scope of this application as there are a wide variety of shapes which may serve the purpose of a sample inlet. The second end 230 of main body 210 may be open, or alternatively, may be sealed with a septum 240, located at the second end 230 or recessed into the main body. Again, note that the second end 230 of main body 210 is shown with a funnel shape, though this particular shape is not intended to limit the scope of this application, and for this first embodiment a wide variety of shapes are possible. Main body 210 has an internal diameter larger than that of needle sheath 60. An outlet port 250 is located toward the second end of main body 210 and can be connected to a pump (not shown).

Figure 5:
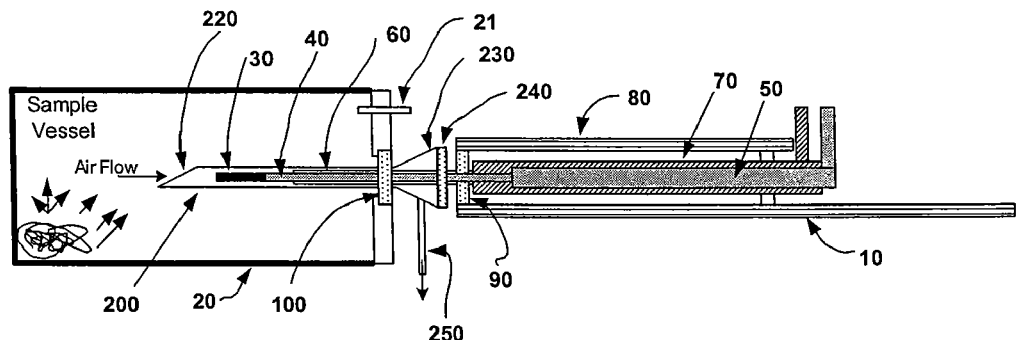
FIG. 5 is another cross sectional view of the first embodiment of an ESD for a SPME after insertion of a needle sheath according to the principles of the present application.

FIG. 5 shows the relative position of SPME 10 and ESD 200 after insertion of needle sheath 60 into ESD 200, with SPME 10 in a fully extended position. Needle sheath 60 has been inserted through septum 90 of SPME 10 and also through (optional) septum 240 of ESD 200, and fiber 30 has been extended through the opening of needle sheath 60. In this way, sample may flow into inlet 220, passing through the main body 210 of ESD 200, in full coaxial contact with fiber 30, and exit ESD 200 via outlet port 250 which can be connected to a pump.

Figure 6A:
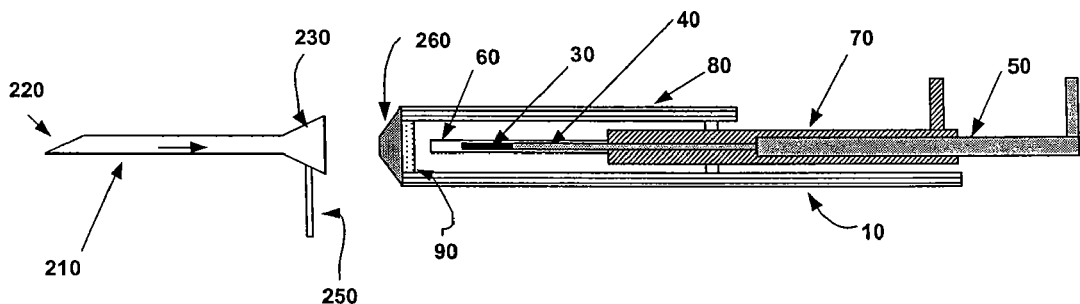
FIG. 6, consisting of FIGS. 6A, 6B, 6C, and 6D, is a cross sectional view of a second embodiment of an ESD for a SPME according to the principles of the present application (FIG. 6A) and various embodiments of an alignment cone therefor (FIGS. 6B-6D)
Figure 6B:
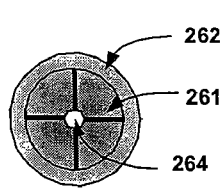
Figure 6C:
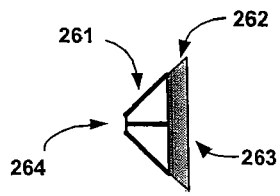
Figure 6D:
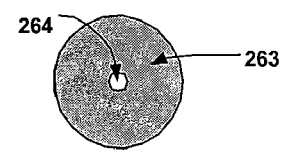

FIG. 6A shows ESD 200 in a second embodiment. In this embodiment, ESD 200 has a funnel-shaped second end 230 and further includes a ribbed alignment cone 260 which attaches to the front of SPME 10 or is manufactured as an integral part of SPME holder 80. Note that this embodiment does not include septum 240 which is optional in the first embodiment. Alignment cone 260, shown in detail in a top view in FIG. 6B, and in a side view in FIG. 6C, has ribs 261 partway down the outermost edge so that the flow can reach and be vented via outlet port 250 which can be connected to a pump. Alignment cone 260 is solid at the wide end 262 to give a gas tight seal with the funnel shaped end 230 of main body 210. The center hole 264 in the alignment cone 260 holds the SPME needle sheath 60 concentric with the ESD body 210. Since the internal diameter of the main body 210 is very small, alignment of SPME needle sheath 60 concentric with the main body 210 can be difficult. The addition of alignment cone 260 makes the alignment easy to accomplish. FIG. 6C shows one embodiment of a side view of the alignment cone 260, showing the ribs 261, the surface 262 which seals with the ESD cone 230, the through hole 264 through which the needle sheath passes, and the rear surface 263 which may be attached over the SPME septum 90. FIG. 6D shows one embodiment of the flat rear surface 263 of the cone which attaches over the SPME septum. Attachment of the cone 260 to the SPME holder 80 can be done with any adhesive compatible with the materials. Another embodiment may use a cone 260 machined such that it is an integral part of SPME holder 80.

Figure 7:
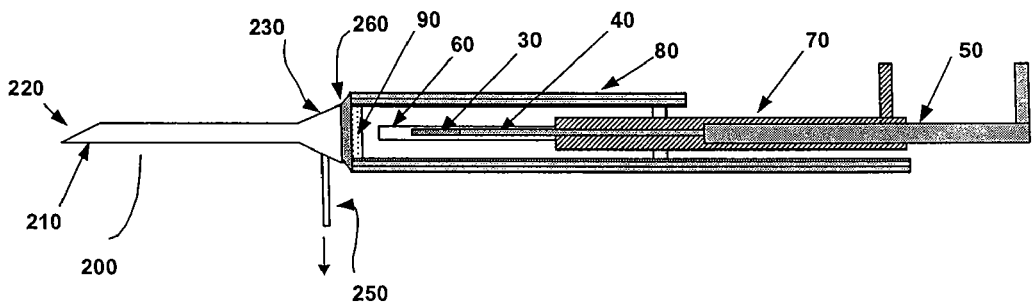
FIG. 7 is a cross sectional view of a third embodiment of an ESD for a SPME according to the principles of the present application.

FIG. 7 shows a third embodiment in which ESD 200 is permanently attached to the front of SPME device 10 as an integrated unit. An alignment cone 260 may optionally be a part of that attachment to insure the proper coaxial alignment of the needle sheath 60 and the ESD body 210 or the ESD 200 may be directly attached to the end of the SPME device 10. The attachment may be accomplished through the use of an adhesive or through other means. In this embodiment ESD 200 may be injected in a sample vessel simultaneously with injection of SPME 10.

Figure 8:
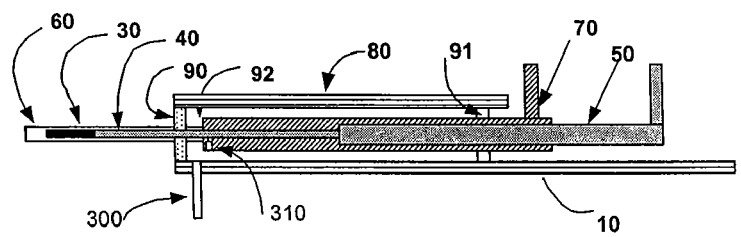
FIG. 8 is a cross sectional view of a fourth embodiment of an enhanced sampling device for a SPME according to the principles of the present application.

FIG. 8 shows a fourth embodiment in which ESD 200 is manufactured integrally to SPME 10. This is accomplished by attaching one end of an outlet port 300 into the side of the body 80 of the SPME 10. The junction of the SPME needle sheath 60 and its rod 70 may be modified to add a vent 310 which may allow gas entering the needle sheath 60 to vent into the sealed internal volume 92 of the SPME and out the vent port 300. In this embodiment the SPME fiber 30 is not extended out of the end of the SPME needle sheath 60. Gaseous or liquid sample is purged through the needle sheath 60 and out of the vent 300 for a metered volume. In this embodiment the SPME needle sheath 60 performs the function of the ESD body 210.

In order to use the present invention in its first embodiment as shown in FIGS. 4 and 5, an operator inserts ESD 200 into sample vessel 20 by piercing septum 100 with first open end 220. The operator then inserts SPME 10 into ESD 200 by aligning needle sheath 60 with main body 210 and depressing cylinder 70, thus injecting needle sheath 60 through optional ESD septum 240 and into main body 210, as shown in FIG. 5. Next, the operator depresses plunger 50 which extends fiber 30 through the free end of needle sheath 60 into main body 210 in proximity to open end 220, thus exposing fiber 30 to the liquid or headspace gas entering main body 210. Alternatively, an automatic insertion device may be used to insert either or both ESD 200 into sample vessel 20 and/or SPME 10 into ESD 200. Alternatively, in another embodiment the ESD 200 can be used with the SPME 10 to sample ambient air without the use of a container.

In order to use the present invention in its second embodiment as shown in FIG. 6, the operator may align and insert funnel-shaped end 230 with alignment cone 260 mounted on front end of SPME 10. At this point, the operator inserts ESD 200 into sample vessel 20. Note that this may be accomplished in one embodiment manually or in another embodiment through the use of an automatic insertion device. The operator then depresses cylinder 70, thus injecting needle sheath 60 through septum 90 and optional ESD septum 240 and into main body 210. Next, in the current embodiment, the operator depresses plunger 50 which extends fiber 30 through the free end of needle sheath 60 into main body 210 in proximity to open end 220, thus exposing fiber 30 to the liquid or headspace gas entering main body 210.

In order to use the present invention in its third embodiment as shown in FIG. 7, the operator may insert ESD 200 into sample vessel 20. Note that this may be accomplished either manually or through the use of an automatic insertion device. The operator then depresses cylinder 70, thus injecting needle sheath 60 through septum 90 and optional ESD septum 240 and into main body 210. Next, in the current embodiment, the operator depresses plunger 50 which extends fiber 30 through the free end of needle sheath 60 into main body 210 in proximity to open end 200, thus exposing fiber 30 to the liquid or headspace gas entering main body 210.

In order to use the present invention in its fourth embodiment as shown in FIG. 8, the operator may position the modified ESD 10 containing the integral vents 300 and 310 over the sample vessel 20. Note that this may be accomplished in one embodiment manually but in another embodiment it may be accomplished through the use of an automatic insertion device. The operator may then depresses cylinder 70, thus injecting needle sheath 60 through septum 90 and into the sample vessel and allowing gaseous sample containing the analyte to flow over fiber 30.

A further application of the ESD includes the sampling of air in proximity to a pipe. The Environmental Protection Agency (EPA) requires that chemical processing plants test all plumbing joints for possible trace leaks, called fugitive emissions. Depending upon the chemical in question, one might wipe the pipe fitting with a treated filter paper for later analysis. One might put a bag over a valve, which contains a dozen possible leak interfaces, and then take an air sample from the bag for a gross leak measurement. One might use a portable analyzer which contains a tube full of chemicals which change color with exposure and a pump to pull air samples through the tube. Since the EPA requires testing of the perimeter of each flange, each bolt perimeter, the valve stem, and any packing nuts around the stem, the ESD may be placed next to an interface (fitting) and retain a sample on the SPME. The ESD/SPME would be easier and more quantitative than the other methods of the prior art.

Further applications include sampling process streams such as duct work for the central air supply of a building, or a line sampling the air in proximity to luggage to detect volatile chemicals. In all of these applications the rate of gaseous flow through the ESD 200 and the time of flow may be used to calculate the total volume of gas passing in close proximity to the SPME fiber. This then allows quantitative reporting of the results in parts of analyte per volume of gas.

It should be apparent to those skilled in the art that the present invention may be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

What is claimed is:

1. A device for enhancing collection efficiency of a sample in combination with a Solid Phase Microextraction (SPME) apparatus for enhancing the flow of an analyte onto a sampling fiber, the SPME apparatus including a tubular housing having a first end closed with a septum,
a rod having a first end,
the sampling fiber attached on one end to the first end of the rod, extending therefrom and having a tip on a second end,
a needle sheath having a bore and open end, the sampling fiber disposed along the bore of the needle sheath, and the rod, the sampling fiber and the needle sheath being reciprocally disposed within the tubular housing,
a first means for maintaining the sampling fiber and the rod in a predetermined fixed position relative to the needle sheath,
a second means for advancing the needle sheath and the rod along the inside of the tubular body until the needle sheath punctures the septum and is exposed beyond the first end of the tubular housing, while maintaining the predetermined fixed position relative to the sampling fiber and the rod,
a third means for advancing the rod and the sampling fiber along the bore of the needle sheath until the fiber tip is exposed beyond the open end of the needle sheath, and
the device for enhancing collection efficiency of a sample comprising:
a main body of a tubular shape with a bore having an inner diameter larger than the outer diameter of the needle sheath, the main body having a first end and a second end, the first end having an opening and the main body having an outlet port proximate to the second end, and
whereby the second end of the main body may be placed in communication with the first end of the tubular housing, and
whereby when the needle sheath and the sampling fiber are exposed beyond the first end of the tubular housing and the sampling fiber tip is subsequently exposed beyond the open end of the needle sheath, the sampling fiber is positioned within the bore of the main body thereby causing the fluid carrying the analyte to pass in close proximity to and coaxially over the surface of the sampling fiber to enhance the flow of the analyte onto the sampling fiber.

2. The device of claim 1, wherein the second end of the main body is sealed with a septum.

3. The device of claim 1, wherein the second end of the main body is open and has a diameter increasing in the direction of the second end, and further comprising an alignment cone permanently attached to the apparatus on the septum of the apparatus, whereby when the second end of the main body is placed in communication with the first end of the tubular housing, the alignment cone fits snugly into the second end of the device.

4. The device of claim 3, wherein the alignment cone is ribbed.

5. The device of claim 1, wherein the second end of the device is attached to the septum of the apparatus.

6. The device of claim 5, wherein the attachment is accomplished with an adhesive.

7. The device of claim 5, wherein the attachment is mechanical.

8. The device of claim 1, wherein the apparatus and the device are permanently attached as an integrated unit.

9. The device as in claims 1, 2, 3, 4, 5, 6 or 7, further comprising a pump connected to the outlet port.

10. The device of claim 1, wherein the analyte molecules are exposed to a capture surface of the sampling fiber.

11. The device of claim 10, further comprising means for quantitatively measuring the volume of gas passing over the exposed sampling fiber.

* * * * *